United States Patent [19]
Levandoski

[11] Patent Number: 5,090,901
[45] Date of Patent: * Feb. 25, 1992

[54] FACE BOW AND ADJUSTABLE OCCLUSAL FORK

[76] Inventor: Ronald R. Levandoski, 1103 Powell Ave., Erie, Pa. 16505

[*] Notice: The portion of the term of this patent subsequent to Jan. 9, 2007 has been disclaimed.

[21] Appl. No.: 461,171

[22] Filed: Jan. 5, 1990

Related U.S. Application Data

[63] Continuation-in-part of Ser. No. 244,098, Sep. 14, 1988, Pat. No. 4,892,480.

[51] Int. Cl.⁵ .................................... A61C 11/00
[52] U.S. Cl. .................................... 433/56; 433/73
[58] Field of Search ................. 433/73, 56, 68, 69

[56] References Cited

U.S. PATENT DOCUMENTS

| | | | |
|---|---|---|---|
| 1,786,915 | 12/1930 | McLean | 433/68 |
| 3,200,497 | 8/1965 | Goodfriend | 433/56 |
| 4,084,319 | 4/1978 | Dragan | 433/73 |
| 4,639,220 | 1/1987 | Nara et al. | 433/68 |
| 4,668,189 | 5/1987 | Levandoski | 433/55 |
| 4,695,252 | 9/1987 | Edwardson | 433/73 |

FOREIGN PATENT DOCUMENTS

| | | | |
|---|---|---|---|
| 2430761 | 3/1980 | France | 433/68 |
| 0143511 | 3/1959 | U.S.S.R. | 433/73 |

*Primary Examiner*—Gene Mancene
*Assistant Examiner*—Adriene B. Lepiane
*Attorney, Agent, or Firm*—Lovercheck and Lovercheck

[57] ABSTRACT

A bracket having a vertical column for supporting a face bow and a bite fork on the face of a patient with impressionable material on the bite fork in the mouth of the patient with the patient's teeth engaging the impressionable material making an impression thereon, and ear engaging members on the face bow engaging the ear openings of the patient, and a lip engaging indicator on the face bow engaging the lip of the patient. The face bow being removable from the bracket and the bracket with facebow removed being adapted to support the bite fork on an articulator, where dentures supported on the articulator can be articulated relative to the impressions on the impressionable material supported on the bite fork.

4 Claims, 4 Drawing Sheets

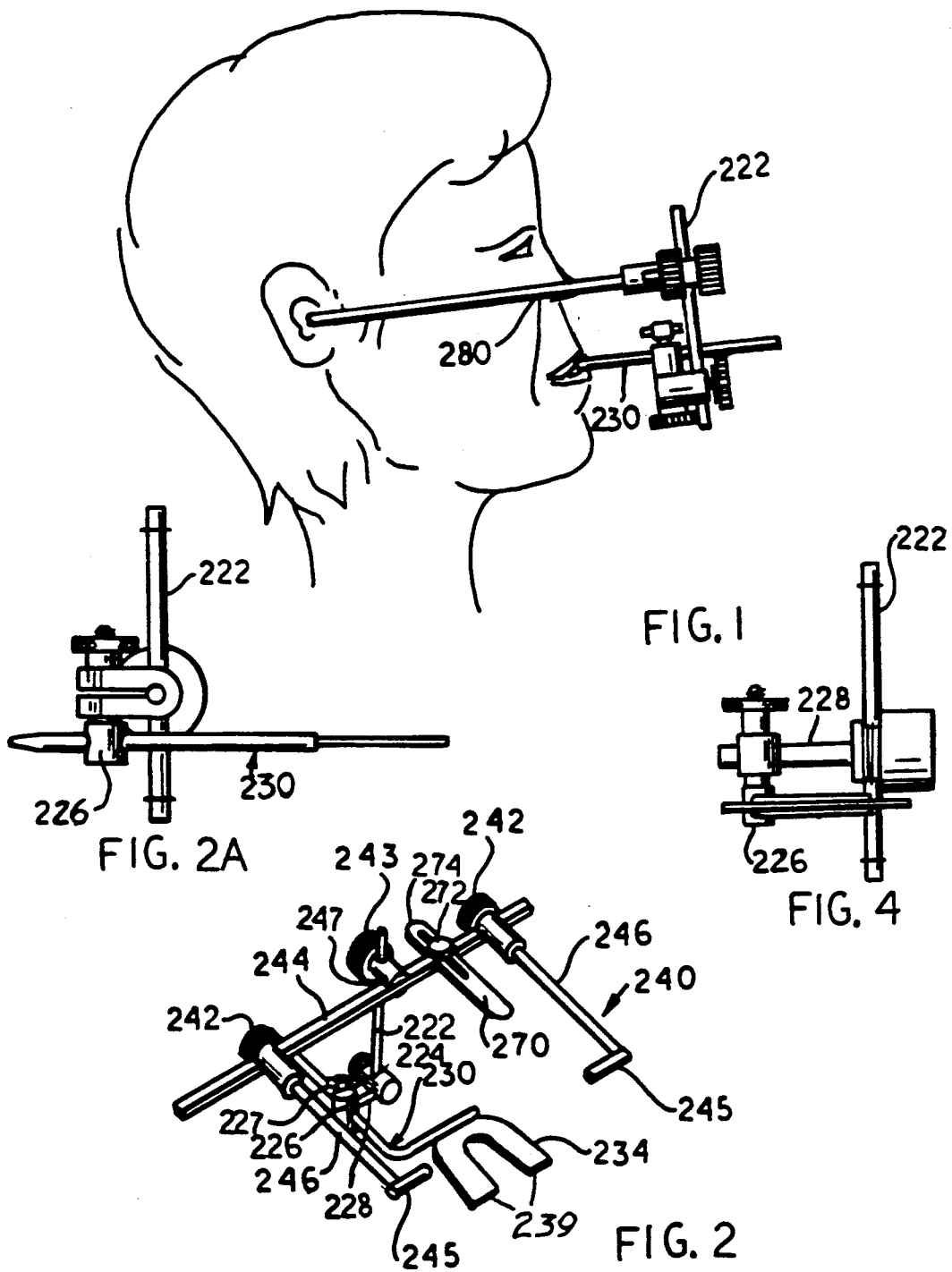

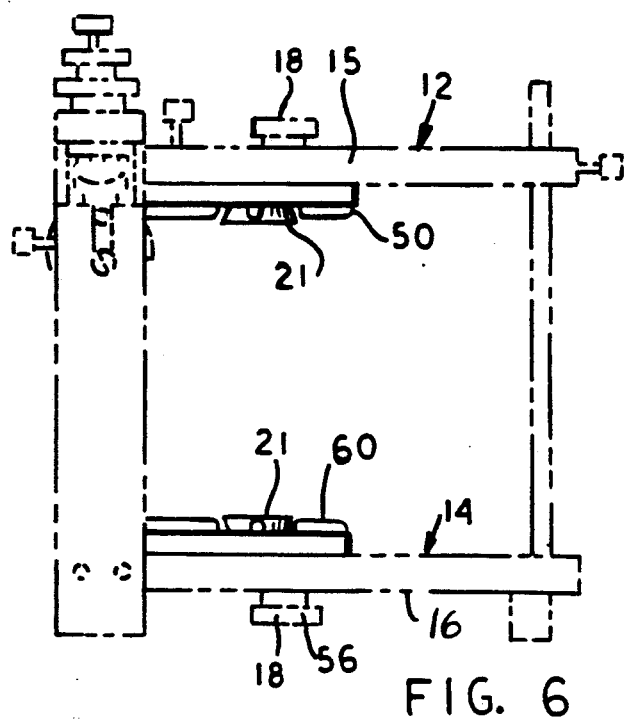
FIG. 6
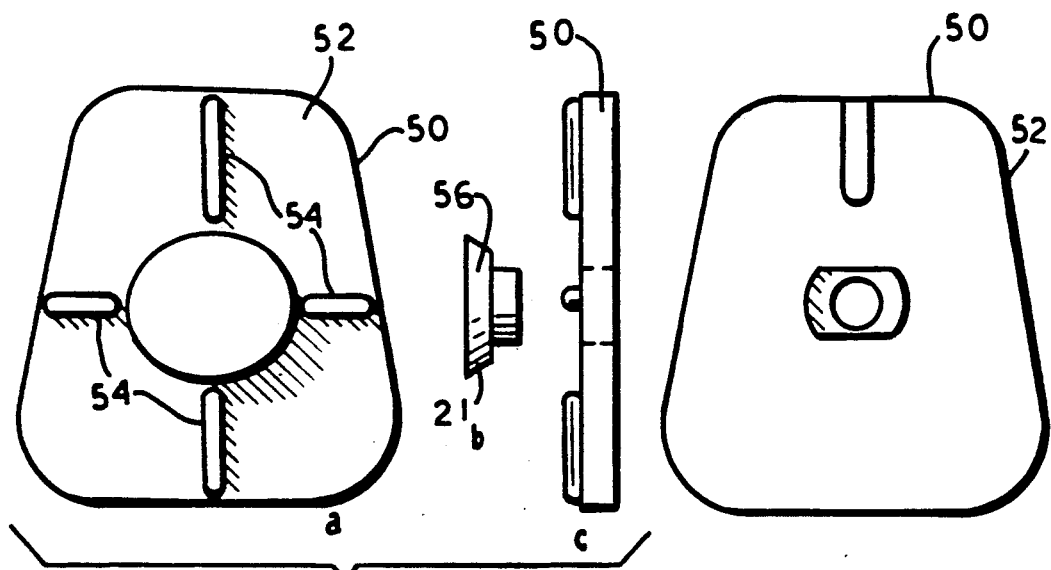
FIG. 7
FIG. 8

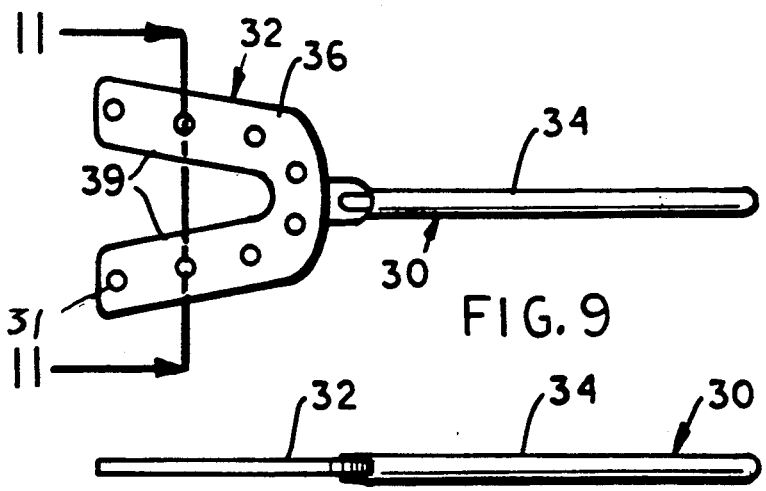
FIG. 9
FIG. 10
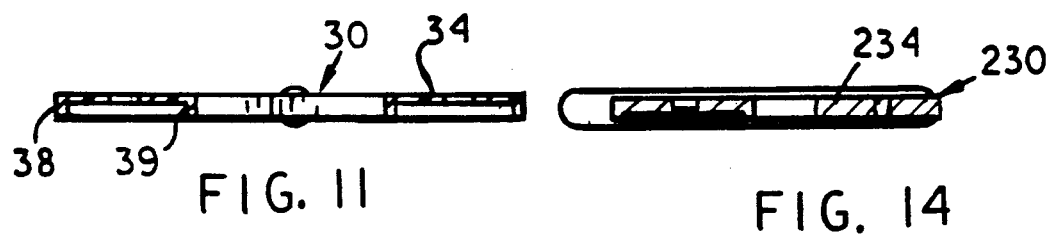
FIG. 11
FIG. 14
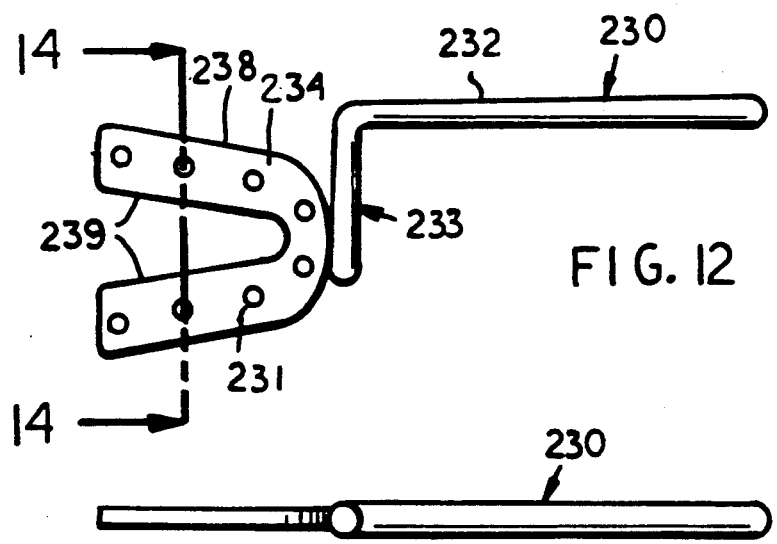
FIG. 12
FIG. 13

FACE BOW AND ADJUSTABLE OCCLUSAL FORK

REFERENCE TO PRIOR APPLICATION

The present invention is a continuation-in-part of U.S. patent application Ser. No. 244,098 filed Sept. 14, 1988 for a face bow, issued on Jan. 9, 1990 as U.S. Pat. No. 4,892,480.

BACKGROUND OF THE INVENTION

In numerous dental and orthodontic procedures, casts are made of the teeth of both the upper and lower jaws of a patient. These dental casts are then mounted on an articulator to reproduce the location and movement of the lower teeth and mandible relative to the upper jaw and maxillary teeth. Various methods of reproducing the teeth for the upper and lower jaws of patients and mounting them in gnathological articulators have been commonly employed in the prior art for a number of purposes, including the making of artificial dentures, gnathological positioners, etc. The importance of using instruments such as articulators is to approximate as closely as possible the patient's opening and closing axis of rotation or arc of closure of the jaws.

It is sufficient in terms of the present invention to understand that the position of patient's teeth in the upper and lower jaws and the relative positioning of the upper and lower jaws must be precisely reproduced in an articulator in order to permit the dentist or orthodontist to determine and carry out the corrective measures which are required for a given patient.

REFERENCE TO PRIOR ART

U.S. Pat. No. 4,695,252 shows a face bow nose indicator and articulator of the type disclosed herein.

Face bows are commonly used in the prior art for transferring maxillary relationship data from patients to such articulators. Also see e.g., U.S. Pat. No. 3,218,716 to Stuart. Present arbitrary face bows are used for recording and relating the patient's jaws and dentition to a universal reference plane and point (ideally the axisorbital plane) oriented relative to the patient's head. These references serve an essential function in properly orienting and transferring spatial information to the dental cast on the articulator.

STATEMENT OF THE INVENTION

This invention relates to dental instruments and more particularly to an occlusal fork and face bow combination.

OBJECTS OF THE INVENTION

The main object of the invention is to provide a novel and improved adjustable bite fork device with a bite palate plate selected in size and shape for an individual palate bite plate.

Another object of the invention is to provide an improved bite fork device.

Another object of the invention is to provide a novel and improved bite fork in combination with an improved face bow and articulator arrangement.

Another object of the invention is to provide an improved face bow.

Another object of the invention is to provide an improved face bow and indicator.

With the above and other objects in view, the present invention consists of the combination and arrangement of parts hereinafter more fully described, illustrated in the accompanying drawing and more particularly pointed out in the appended claims, it being understood that changes may be made in the form, size, proportions and minor details of construction without departing from the spirit or sacrificing any of the advantages of the invention.

BRIEF DESCRIPTION OF THE DRAWINGS

FIG. 1 is a side view of the face bow shown on a patient.

FIG. 2 is an isometric view of the face bow, bite fork and reference means on a support bracket.

FIG. 2A is a side view of the bite fork on the bracket of FIGS. 1, 2 and 3.

FIG. 4 is another side view of the bite fork on the bracket of FIGS. 1, 2 and 3.

FIG. 6 is a side view of the denture supports on an articulator according to the invention.

FIG. 7 is a top and bottom view of one of the denture supports of FIG. 6.

FIG. 8 is a bottom view of the denture support.

FIG. 9 is a top view of a bite fork according to the invention.

FIG. 10 is a side view of the bite fork shown in FIG. 9.

FIG. 11 is a cross sectional view taken on line 11—11 of FIG. 9.

FIG. 12 is a top view of another embodiment of the bite fork.

FIG. 13 is a side view of the embodiment of the invention shown in FIG. 12.

FIG. 14 is a cross sectional view taken on line 14—14 of FIG. 12.

DETAILED DESCRIPTION OF DRAWING

Figure 3:
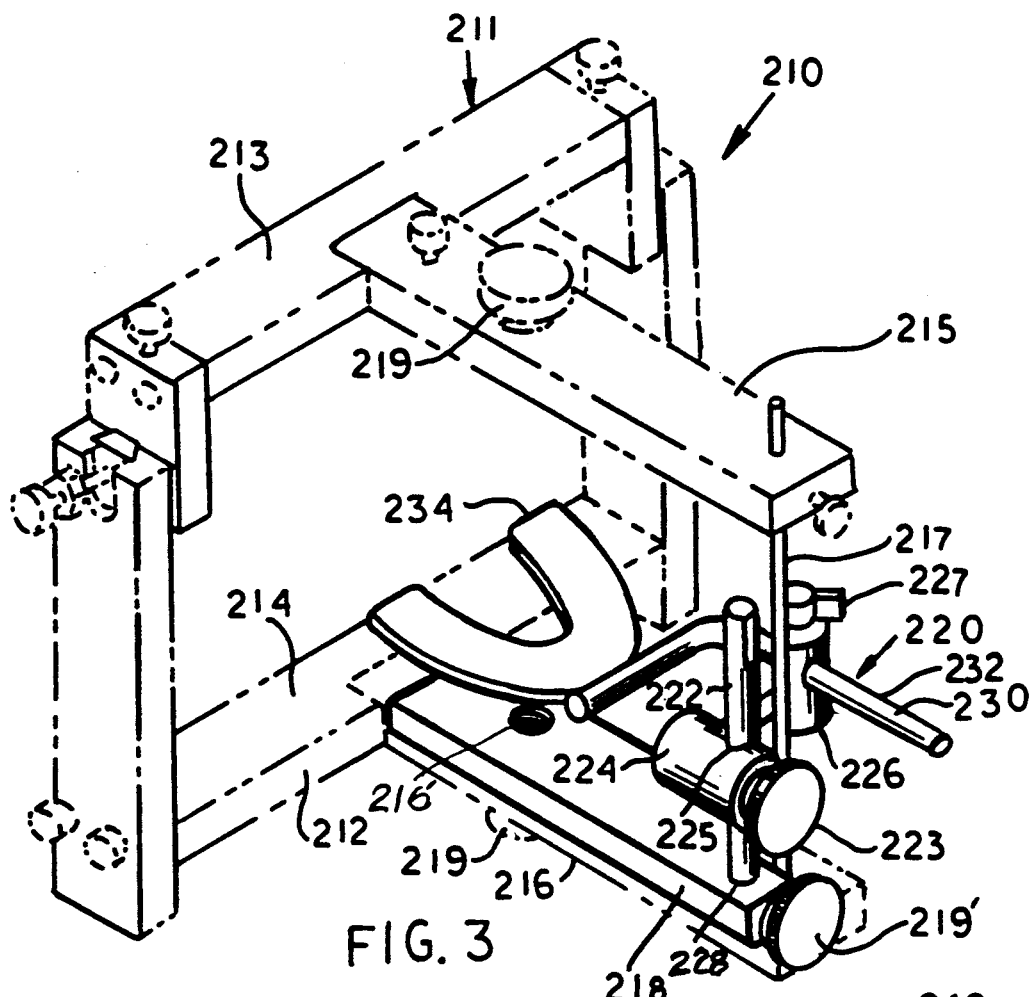
FIG. 3 is a isometric view of the bite fork and support bracket shown in FIG. 2 supported on an articulator shown in phantom.
Figure 5:
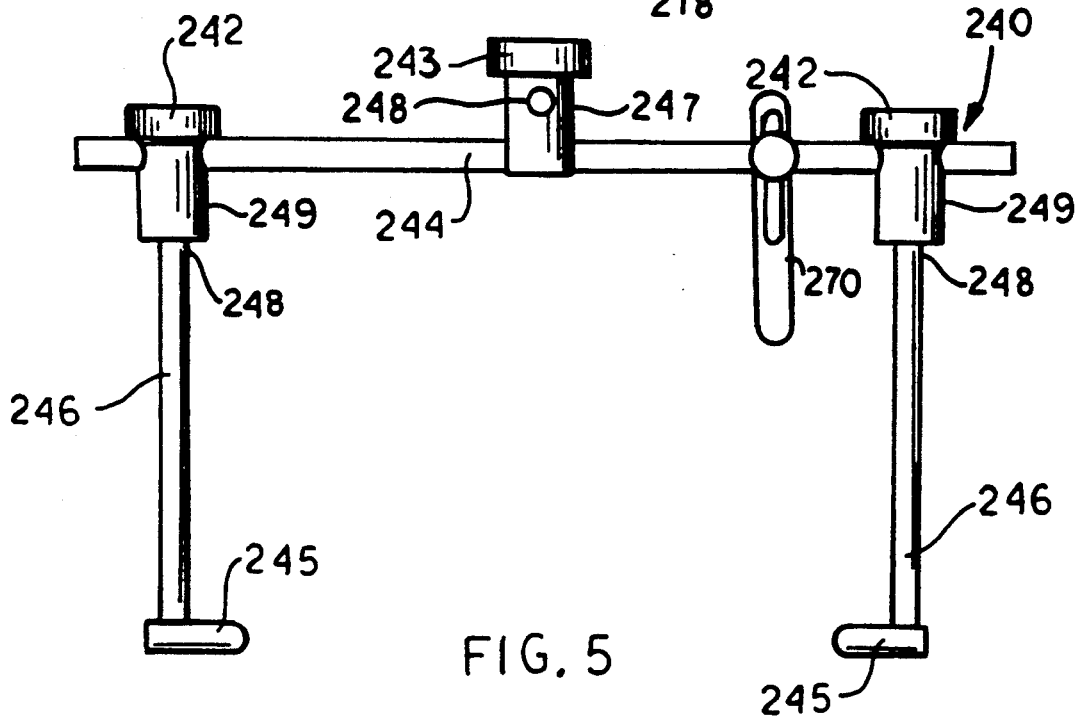
FIG. 5 is a top view of the calipers according to the invention.

Now with more particular reference to the drawings, FIG. 1 shows the combination of bracket means 220 supporting bite fork 230 and face bow 240 supported on the face of a patient. Bite fork 230 may support an impressionable material adjacent the patient's teeth to get a tooth impression for use with dentures supported on articulator 210. Such impressionable material for dental use is familiar to those skilled in the art. Bite fork 230 and face bow 240 are referenced to the patient's face by indicator means 270 which has set screw 272 in slot 274 by which indicator means 270 may be adjusted to engage the patient's face adjacent the upper lip and nostril, thereby, referencing bracket 220 and bite fork 230 to the patient's face.

The combination shown in FIG. 1 is shown in greater detail in FIGS. 2, 2A and 4. Support bracket 220 is made up of column 222 of lateral rod 228, lower clamp 224 and lateral clamp 226. Lower clamp 224 has first vertical bore 225 that receives column 222 and set screw 223 which locks column 222 in a vertical position.

A lateral bore in clamp 224 receives lateral rod 228 and clamp stud 227 locks bite fork pin 232. Face bow 240 is supported on the upper end of column 222. Stud 243 locks upper clamp 247 in a vertical adjusted position on column 222.

Bite fork 230, shown in FIGS. 1-4, 12 and 13, has bifurcated plate 234 fixed to lateral pin part 233 which is a part of bite fork pin 232. Bite fork pin 232 is received in lateral clamp 226 and is locked in adjusted position in clamp 226 by a suitable set screw. Bite fork 230 has a space between fork members 239 and is adapted to support an impressionable material. The impressionable material is adapted to receive impressions from the patient's teeth when supported on the patient's face as in FIG. 1.

Face bow 240 is a generally U-shaped member made up of transverse bar 244 and side arms 246 which extend generally perpendicular to transverse bar 244. Transverse bar 244 is supported on column 222 by first bracket 247 and side arms 246 are adjustably attached to transverse bar 244 by second and third brackets 249. The distal ends of side arms 246, remote from transverse bar 244 have ear pieces 245 fixed thereto. Second and third bracket 249 are both slidably supported on transverse bar 244 and may be locked in place by screws 242. Side arms 246 may have threaded ends 248 threadably received in second and third brackets 249. Ear pieces 245 may have removable plastic tips that can be sterilized.

The articulator 210 shown in FIG. 3 is similar to the articulator shown in U.S. Pat. No. 4,668,189. The articulator has upper frame 211. Pivoted to lower frame 212 as shown and explained in U.S. Pat. No. 4,668,189, upper beam 213 which has arm 215, and lower beam 216 which has adapter plate 218 to attached lower arm 216 to receive column 222.

The embodiment of the articulator shown in FIG. 6 is shown without the adapter plate. The denture support plates shown in FIG. 6 will be supported in the same manner as shown in the embodiment of FIG. 3.

The embodiment of bite fork 30 shown in FIGS. 9 and 10 has bifurcated plate 32 with legs 39 which corresponds to bifurcated plate 234 in the embodiment of FIGS. 11 through 14. Pin 34 is straight as compared with bite fork pin 232 which has a branch 233. Bifurcated plate 32 has holes 31 while bifurcated plate 234 has holes 231 to better support an impressional material on it. Flange 38 on bifurcated plate 32 extends downward to aid in holding the impressionable material. The embodiment of FIGS. 11 through 14 could also have a flange like flange 38.

First denture support pad 50 is supported on articulator arm 15. First denture support pad 50 is made up of flat plate-like member 52. Ribs 54 are supported on the top of flat plate-like member 52 to better support the dentures. Ribs 54 radiate from the center of first denture support pad 50 and second denture support pad 60. Threaded members 21 are provided on arms 12 and 14 on the articulator for receiving threaded members 21 for clamping first denture support pad 50 and second denture support pad 60 to arms 15 and 16 on the articulator respectively. Similar structures will clamp support pads to arm 215 in the embodiment of the articulator shown in FIG. 3.

In operation an impressionable material is placed on bifurcated plate 234 or bifurcated plate 32 and bracket means 220 with bite fork 230 and face bow 240 are supported on column 222 of bracket means 220 as shown in FIG. 2 and mounted on the face of a patient, as shown in FIG. 1. Indicator 270 is adjusted to engage the patient's face to indicate the relative position of bifurcated plate 234 to the patient's face. An impression of the patient's teeth is taken in the impressionable material. Face bow 240 is then removed from column 222 and bracket means 220 with bite fork 230 on bracket means 220 is transferred to articulator 210 and column 222 is supported on adapter plate 218. Column 222 is received in hole 228 in adapter plate 218, which is a plate-like member that rests on lower beam 216. Screw 219' clamps column 222 in place in adapter plate 218. Adapter plate 218 is held in place on lower beam 216 by screw 219 and engages threaded hole 216' in adapter plate 218. Dentures supported on first denture support pad 50 and second denture support pad 60 are adjusted on articulator 210 by adjusting their position to align the dentures with the impression in the material supported on bifurcated plate 234.

The foregoing specification sets forth the invention in its preferred, practical forms but the structure shown is capable of modification within a range of equivalents without departing from the invention which is to be understood is broadly novel as is commensurate with the appended claims.

The embodiments of the invention in which an exclusive property or privilege is claimed are defined as follows:

1. In combination an articulator, a bracket means, a bite fork, a face bow and a vertically extending column,
   said articulator having a lower frame and an upper frame,
   pivot means connecting said upper frame to said lower frame,
   a first denture support on said lower frame,
   a second denture support on said upper frame,
   said face bow being a generally U-shaped member comprising a transverse bar,
   said transverse bar having a first end, a second end and an intermediate part,
   a first bracket attached to said intermediate part of said transverse bar and slidably and adjustably supported on said vertically extending column,
   said first bracket having a screw for locking said first bracket in position on said vertically extending column,
   a first side arm and a second side arm,
   a second bracket slidably and adjustably supported on said transverse bar adjacent said first end,
   a third bracket slidably and adjustably supported on said transverse bar adjacent said second end,
   said second bracket and said third bracket each having a screw for locking each said bracket in place on said transverse bar,
   first attaching means for attaching said first side arm to said second bracket,
   second attaching means for attaching said second side arm to said third bracket and slidably supported on said transverse bar adjacent said second end,
   ear pieces on said first side arm and said second side arm,
   said ear pieces being adapted to have removable sterilizable plastic tips thereon,
   fourth bracket means supporting said bite fork on said column on said patient's face,
   indicating means on said face bow for engaging the face of a patient adjacent an upper lip and nostril of said patient,
   said bite fork being adapted to have impressionable material supported thereon whereby said bite fork can be inserted into the mouth of a patient for taking an impression of said patient's teeth, said bite fork being adapted to be adjusted by said second bracket and by said third bracket to conform to said patient's face with said patient impressing said impressionable material with his teeth, said face bow being adapted to be removed from said fourth bracket means, said fourth bracket means with said bite fork and said impressioned material being adapted to be transferred to said articulator and support means on said lower frame of said articulator for supporting said fourth bracket means and said bite fork to articulate dentures to conform to said impression in said impressionable material, thereby allowing said dentures to be adjusted to conform to said patient's teeth impressions on said impressionable material on said bite fork.

2. The combination recited in claim 1 wherein said fourth bracket means [220] comprises said vertical column [222] and a first clamp [224] supported on said vertical column [222], a lateral rod [228] supported on said first clamp [224], a second clamp [226] being supported on said lateral rod [228], said bite fork [230] having a pin [232] and a bifurcated plate [234] supported on said pin [232], said pin being supported on said second clamp.

3. The combination recited in claim 1 wherein said vertically extending column is in the form of a generally round column, an adapter plate on said lower frame, said support means comprising a hole in said adapter plate receiving a lower end of said column.

4. The combination recited in claim 1 wherein said first attaching means and said second attaching means comprise first threaded ends on said first side arm and second threaded ends on said second side arm threadably received in said second bracket and in said third bracket.

* * * * *